US005243661A

United States Patent [19]

[11] Patent Number: 5,243,661

[45] Date of Patent: Sep. 7, 1993

Ohkubo et al.

[54] MICROPHONE APPARATUS

[75] Inventors: Masashi Ohkubo; Tooru Sasaki, both of Tokyo; Yasushi Katsumata; Akira Kimura, both of Kanagawa, Japan

[73] Assignee: Sony Corporation, Tokyo, Japan

[21] Appl. No.: 680,408

[22] Filed: Apr. 4, 1991

[30] Foreign Application Priority Data

Apr. 9, 1990 [JP] Japan .................................... 2-93701
Apr. 12, 1990 [JP] Japan .................................... 2-97083

[51] Int. Cl.[5] ...................... H04B 15/00; A61F 11/06; H04R 3/02

[52] U.S. Cl. ........................................ 381/94; 381/71; 381/73.1

[58] Field of Search .................... 381/71, 73.1, 93, 94, 381/13

[56] References Cited

U.S. PATENT DOCUMENTS 4,329,714 5/1982 Pritchard .............................. 381/94
4,377,793 3/1983 Horna .................................. 381/71
4,589,137 5/1986 Miller .
4,658,426 4/1987 Chabries et al. ...................... 381/94
4,723,294 2/1988 Taguchi ............................... 381/94
4,769,847 9/1988 Taguchi ............................... 381/94

OTHER PUBLICATIONS

Patent Abstracts of Japan, vol. 6, No. 79 (P-115) May 18, 1982.

Patent Abstracts of Japan, vol. 11, No. 23, (E-473), Jan. 22, 1987 Publication No. JP 61194914.

*Primary Examiner*—James L. Dwyer
*Assistant Examiner*—Jack Chiang
*Attorney, Agent, or Firm*—Lewis H. Eslinger; Jay H. Maioli

[57] ABSTRACT

A microphone apparatus having a microphone for producing a desired audio signal, includes an adaptive signal processing section which is supplied with a reference signal based on a vibration detected signal from a vibration detecting circuit in response to a vibration of a vibration generating source whose vibration is picked up by the microphone and becomes an unnecessary noise signal, or in response to a control signal for controlling a drive source of a driving unit of a recording apparatus for recording an output signal from the microphone and which reduces a noise signal contained in the audio signal.

5 Claims, 9 Drawing Sheets

MICROPHONE APPARATUS

BACKGROUND OF THE INVENTION

1. Field of the Invention

The present invention generally relates to microphones and, more particularly, is directed to a microphone apparatus suitable for reducing an unnecessary noise signal by adaptive signal processing.

2. Description of the Prior Art

In a recorder such as a video tape recorder having a built-in type camera or the like, the microphone picks up and produces unnecessary noise signals generated from an inner (mechanical system) or outer vibration generating source in addition to the desired audio signal.

That is, the microphone picks up vibration (inner vibration) of a driving section of the video tape recorder to produce noise. For example, when a recorder is placed on a desk and when any vibration (external vibration) is applied to the desk, the vibration is picked up as noise.

To solve this problem, the microphone is designed to have directivity with a low sensitivity to the noise and mounted to be positioned as far as possible from the noise source. However, since the noise reduction is not enough, the noise is also reproduced as audible sounds. Also, when an external vibration is directly applied to the microphone, the vibration is picked up as noise.

To overcome this disadvantage, the adaptive signal processing is known, in which the noise signal picked up and produced from the microphone is electrically processed and reduced. As will be understood from FIG. 1, an adaptive filter 11 used in the adaptive signal processing includes (K-1) delay elements (for every clock) 20 . . . and K variable amplifiers 30

The first amplifier 30 (leftmost one in FIG. 1) is directly supplied with a reference signal n; and the succeeding amplifiers 30 are respectively supplied with the reference signal $n_1$ through the respective delay elements 20.

Assuming that $W_k$ is the coefficient of the adaptive filter 11 and also assuming that t is time and that t-1 is the time of one preceding clock, then the following equation (1) will be established between coefficients $W_{k,t}$ and $W_{k,t-1}$:

$$W_k = W_{k,t-1} + 2\mu\epsilon_{t-1} x N_{1\,k,t-1} \quad (1)$$

Then, the coefficients W: are changed, and each time they are changed, a filter associated with the reference signal $n_1$ is formed.

The adaptive filter 11 is proposed in B. Widrow and S. D. Stearns: "Adaptive Signal Processing", Prentice-Hall, 1985, and in Digital signal processing - advanced course, <adaptive signal processing>, Journal of 35th Technical Lecture Meeting held by Acoustical Society of Japan, etc.

In the adaptive signal processing, however, the amount of noise signal reduction depends on a reference signal necessary for such processing, and thus there is a problem of how to select the reference signal.

OBJECTS AND SUMMARY OF THE INVENTION

Accordingly, it is an object of the present invention to provide an improved microphone apparatus in which the aforenoted shortcomings and disadvantages of the prior art can be eliminated.

More specifically, it is an object of the present invention to provide a microphone apparatus in which a vibration detected signal from a vibration source provided within or out of a recorder to produce noise is used as a reference signal to perform adaptive signal processing, so that noise reduction can be properly made.

Another object of the present invention is to provide a microphone apparatus in which a drive source control signal of a recorder is used as a reference signal to perform adaptive signal processing, so that noise reduction can be properly made.

As a first aspect of the present invention, a microphone apparatus is comprised of a microphone for producing a desired audio signal, a vibration detecting circuit for producing a vibration detected signal in response to a vibration of a vibration generating source which generates a vibration picked up by the microphone to produce an unnecessary noise signal, and an adaptive signal processing section supplied with the vibration detected signal as a reference signal and that acts to reduce the noise signal contained in the audio signal.

As a second aspect of the present invention, a microphone apparatus is comprised of a microphone for supplying a desired audio signal to a recording apparatus having a driving unit, and an adaptive signal processing section for reducing an unnecessary noise signal of noise generated from the driving unit, picked up and produced by the microphone on the basis of a predetermined reference signal, wherein the adaptive signal processing section is supplied with a control signal supplied to a driving source of the drive unit as the reference signal.

As a third aspect of the present invention, a recording apparatus having a recording mechanism for recording an output signal from a microphone is comprised of a vibration detecting circuit for producing a vibration detected signal in response to a vibration of a vibration generating source which generates a vibration picked up by the microphone to produce an unnecessary noise signal, and an adaptive signal processing section supplied with the vibration detected signal as a reference signal and reducing the noise signal contained in the audio signal.

In accordance with a fourth aspect of the present invention, a recording apparatus having a recording mechanism for recording an output signal from a microphone is comprised of an adaptive signal processing section for reducing an unnecessary noise signal of noise generated from the driving unit, picked up and produced by the microphone on the basis of a predetermined reference signal, wherein the adaptive signal processing section is supplied with a control signal supplied to a driving source of the drive unit as the reference signal.

The above and other objects, features and advantages of the present invention will become apparent in the following detailed description of illustrative embodiments thereof to be read in conjunction with the accompanying drawings, in which like reference numerals are used to identify the same or similar parts in the several views.

DESCRIPTION OF THE PREFERRED EMBODIMENTS

The preferred embodiments of the microphone apparatus according to the invention will now be described with reference to the accompanying drawings.

Figure 1:
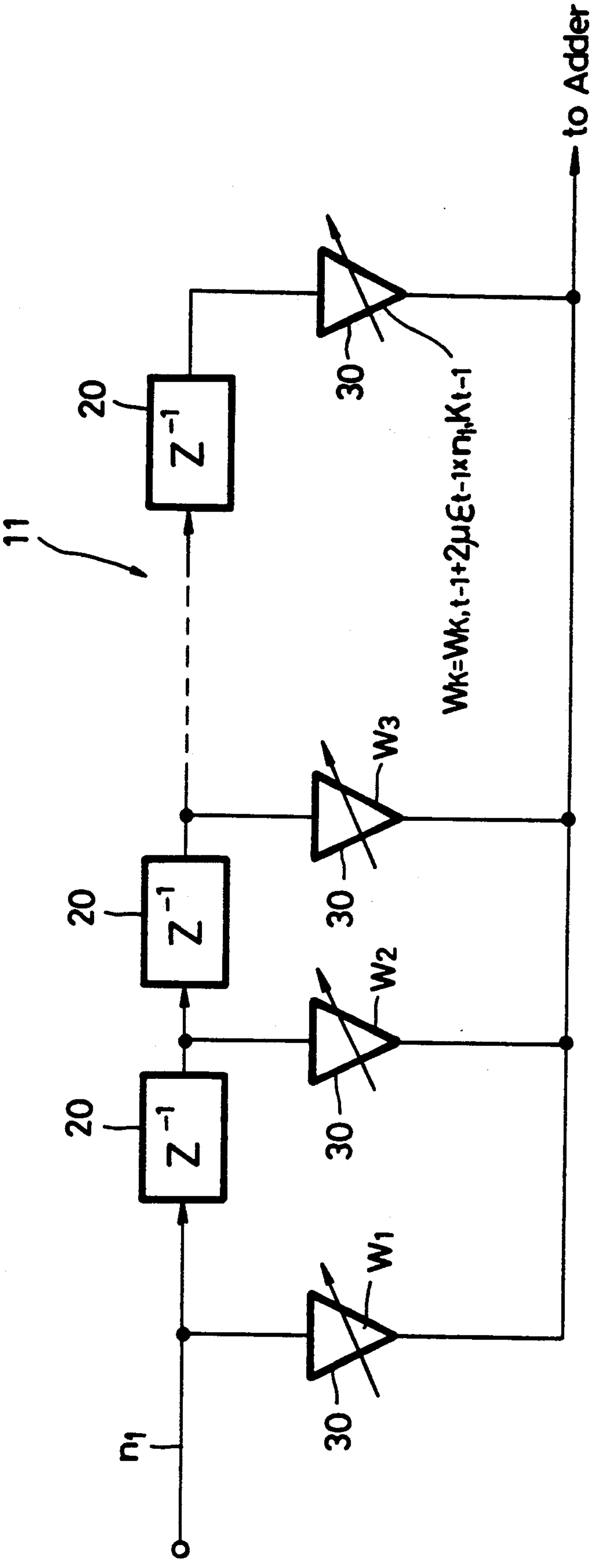
FIG. 1 is a conceptual diagram of an adaptive filter, and to which references will be made in explaining the function of this adaptive filter.
Figure 2:
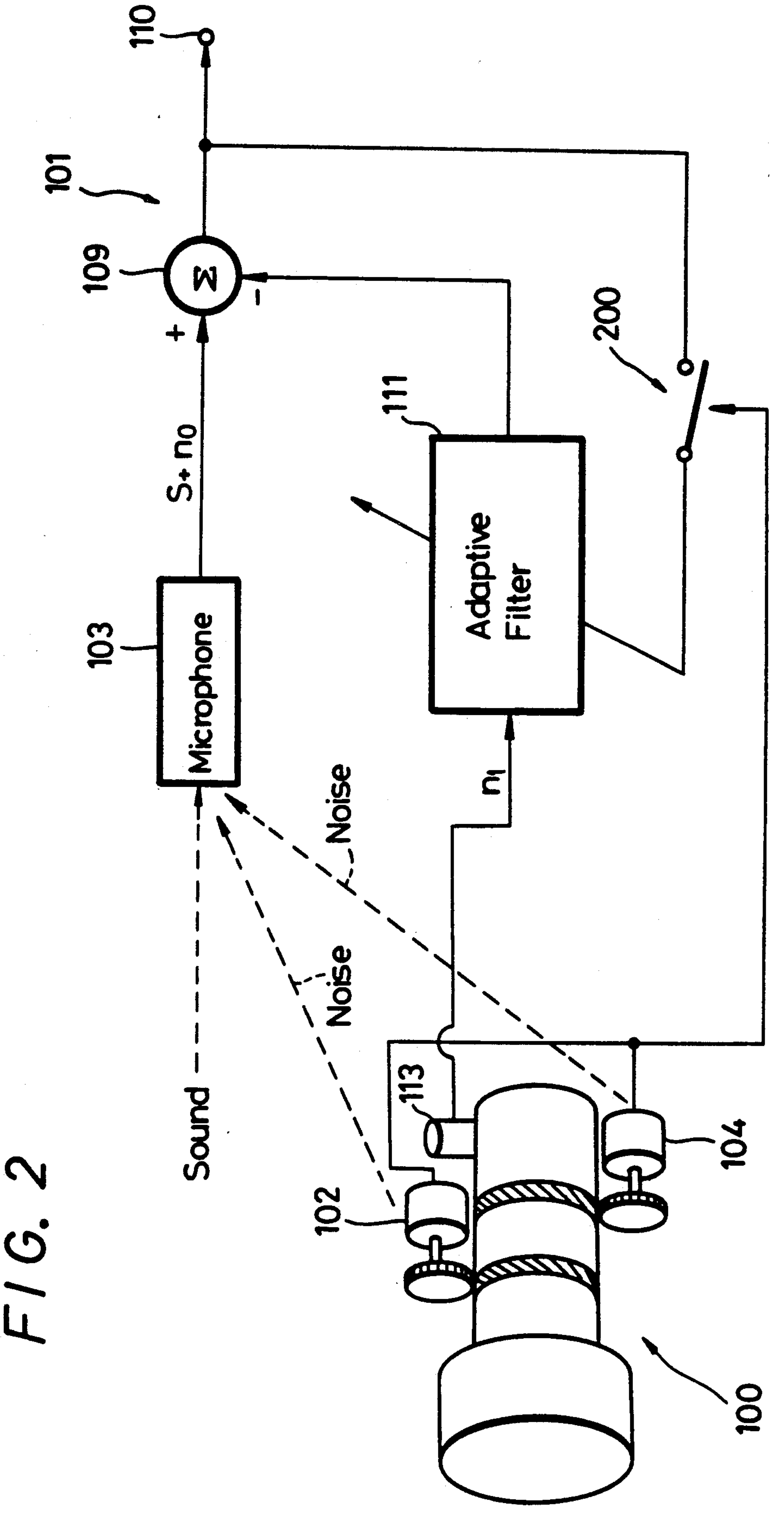
FIG. 2 is a schematic diagram showing an arrangement of a first embodiment of a microphone apparatus according to the present invention.

FIG. 2 generally shows a schematic block diagram of a microphone apparatus 101 to which the present invention is applied. A microphone 103 picks up a desired sound such as a human voice or the like and produces an audio signal S, and the microphone 103 also picks up noise (vibration) generated from a vibration generating source and produces a noise signal $n_0$.

The audio signal S and the noise signal $n_0$ are mixed and supplied to an adder 109, and the output of the adder 109 is supplied to a recording system, not shown, through a terminal 110 and also to an adaptive filter 111 through a switch 200.

Vibration may generally be generated when the drive unit of, for example, a video tape recorder having a built-in camera in which the above-mentioned microphone apparatus 101 is provided is operated (vibration is generated from the internal side); and when a vibration is applied to a desk on which the microphone apparatus 101 is placed (e.g., if a person taps the desk, a vibration is generated from the outside).

Figure 3:
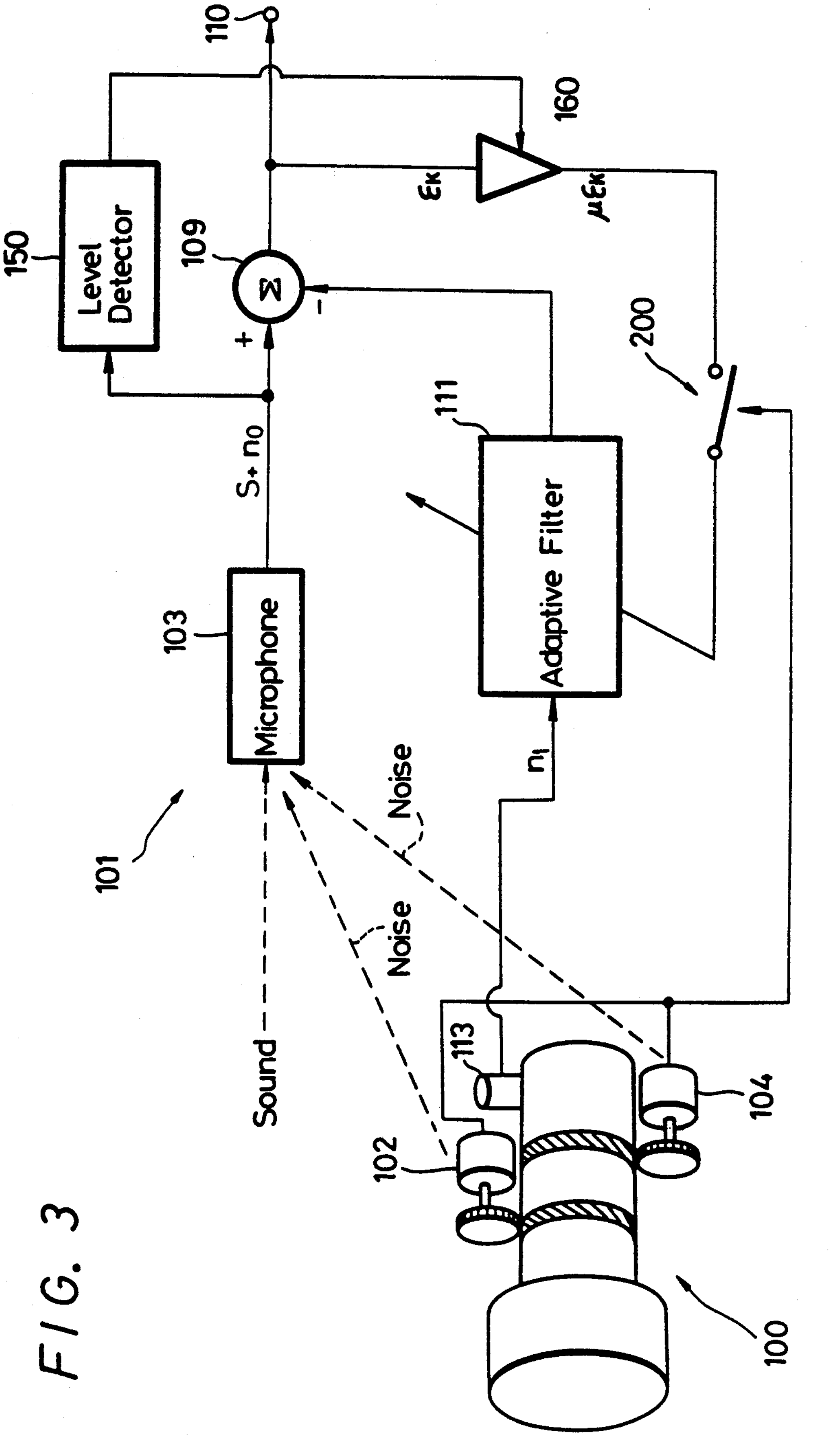
FIG. 3 is a schematic diagram showing an arrangement of a second embodiment of a microphone apparatus according to the present invention.
Figure 4:
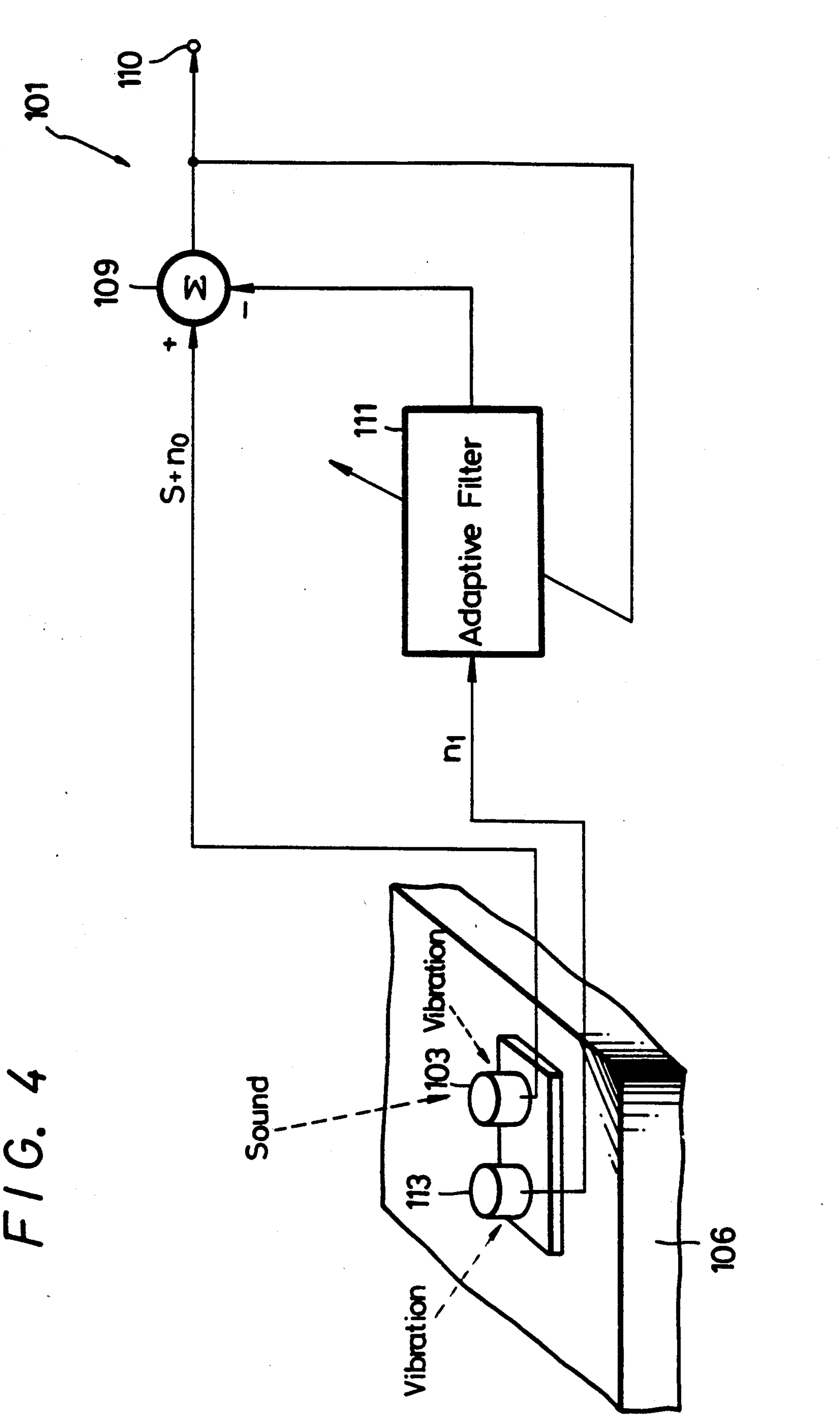
FIG. 4 is a schematic diagram showing an arrangement of a third embodiment of the microphone apparatus according to the present invention.

Accordingly, vibration detecting means (pickup) 113 formed of piezoelectric elements or the like which respond to the vibration from the vibration generating source generate a vibration detected signal $n_1$ is located as shown in FIGS. 2 and 3 at a position so as to detect the vibration generated from the inside, for example, from an auto-focusing motor 102 and a zooming motor 104 of, for example, the video tape recorder having a built-in camera 100 (i.e., near the motor or the gear), and as shown in FIG. 4 at a position to detect the vibration generated from the outside, or the desk 106.

Figure 5:
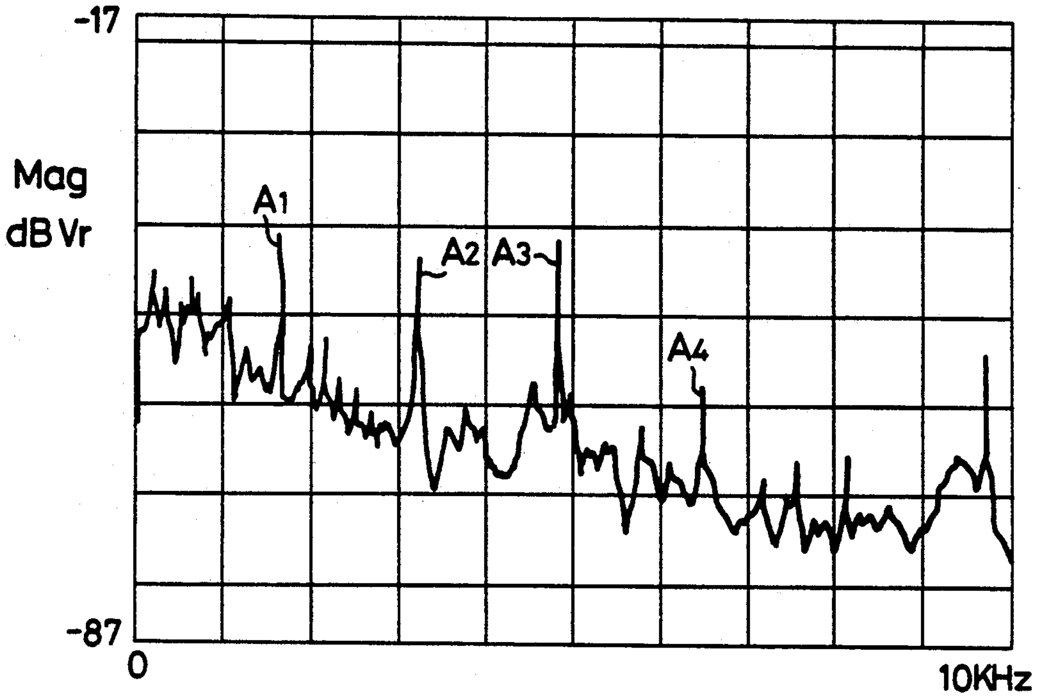
FIG. 5 is a correlative diagram showing a spectrum provided when a video tape recorder having a built-in camera is in the recording mode.
Figure 6:
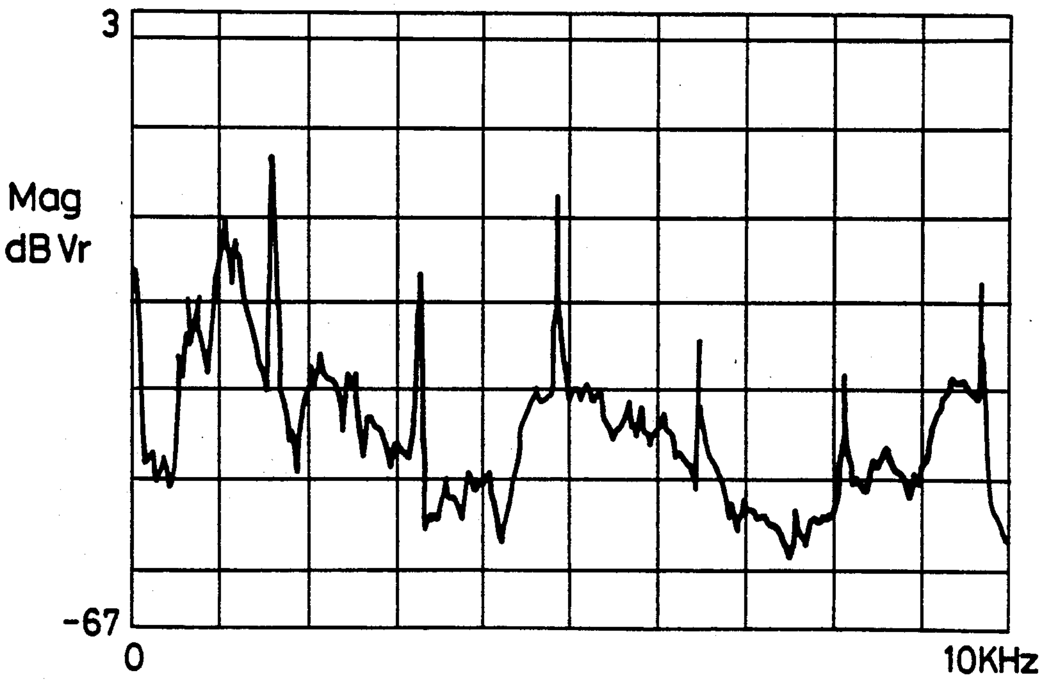
FIG. 6 is a correlative diagram showing a spectrum of a signal $n_1$.
Figure 7:
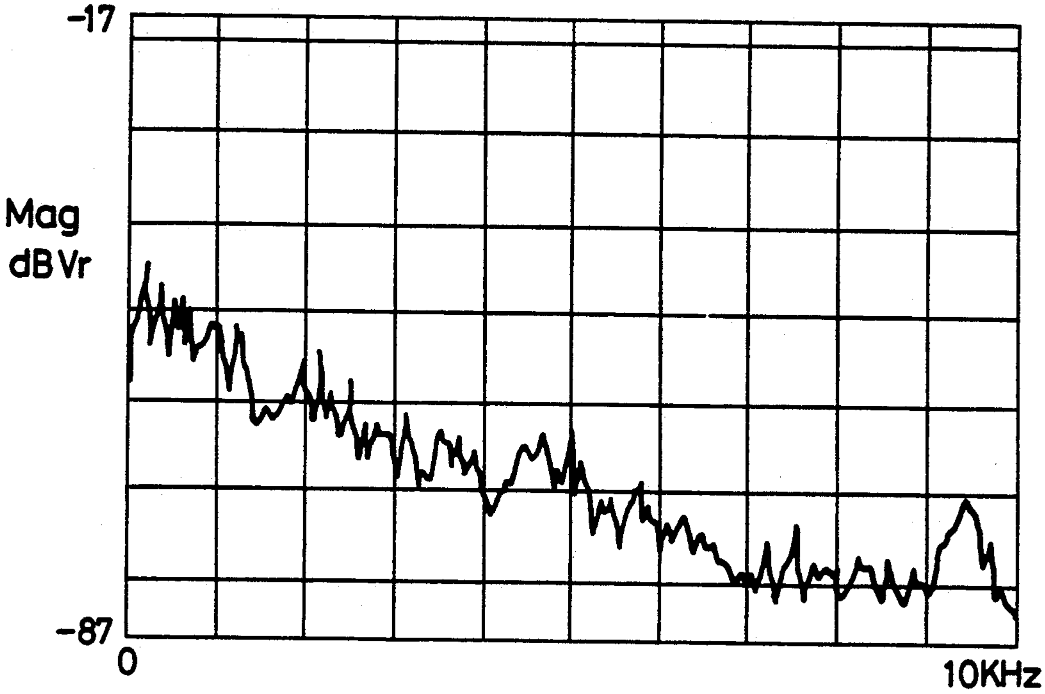
FIG. 7 is a correlative diagram showing a spectrum of a signal processed by an adaptive signal processing circuit.

As will be understood from FIG. 5, when the video tape recorder having a built-in camera 100 is in the recording mode (pickup 113 is mounted on a flexible board mounted on a rotary drum), a noise signal $n_0$ having a spectrum having peak values $A_1$, $A_2$, $A_3$ and $A_4$ is generated. The spectrum of the signal $n_1$ produced from the output of the pickup 113 has a plurality of peak values $A_1$, $A_2$, $A_3$ and $A_4$ as shown in FIG. 6. However, these peak values are removed by the adaptive signal processing in the adaptive filter 111 or the like (adaptive signal processing unit) from the spectrum of the noise signal $n_0$ which is produced from the video tape recorder having a built-in camera 100 as will be understood from FIG. 7.

As described above, according to the above embodiments, the output signal $n_1$ of the pickup 113 is used as the reference signal $n_1$ so that the peak values $A_1$, $A_2$, $A_3$ and $A_4$ of the noise signal $n_0$ are removed by the adaptive signal processing unit such as the adaptive filter 111 or the like.

Consequently, the noise signal $n_0$ is properly reduced and thus, the audio signal is satisfactorily reproduced.

As will be seen from FIGS. 2 and 3 which respectively shown the first and second embodiments of the present invention, when the pickup 113 detects the vibration of the auto-focusing motor 102 or the zooming motor 104, a switch 200 is interposed between the output terminal of the adder 109 and the input terminal of the adaptive filter 111 and the switch 200 is closed only when the auto-focusing motor 102 or the zooming motor 104 is driven. Thus, since the adaptive signal processing is effected only when the motor 102 or the motor 104 is driven, the auto-focusing driving sound and the zooming driving sound are reliably removed and useless power consumption is suppressed, thus the adaptive signal processing being effectively performed.

In addition, when the noise signal $n_0$ is reduced, for example, in an analog circuit, the gain adjustment in the microphone 103 and the pickup 113 is difficult, and the noise signal $n_0$ is not reduced enough if the adjustment is inappropriate, but in this embodiment, the adaptive signal processing is performed so that the noise signal $n_0$ can be easily and reliably reduced.

Further, even though the reproduced sound from the speaker contains, for example, both musical sound and noise, it is frequently observed that human auditory sense cannot distinguish the noise from the musical sound if the volume of the musical sound exceeds a certain level.

Therefore, in this case, the adaptive signal processing is not necessarily performed and the adaptive signal processing may be performed only when the level of musical sound, or the level of the audio signal S, is below a certain level.

In other words, such construction may be taken that the adaptive signal processing is performed only when the level of the audio signal (containing the noise signal $n_0$) is below a certain "threshold value". and that the level of the "threshold value" is properly selected or set in accordance with the kind (human voice, music and so on) of the audio signal S or the like.

As will be understood from FIG. 3, in this case, the output of the microphone 103 is supplied to a level detector 150, wherein the level thereof is detected, and the output of the level detector 150 is supplied to an amplifier 160 for changing the amplification factor $\mu$ of the amplifier 160.

The output $\epsilon k$ of the adder 109 is amplified into $\mu\epsilon k$ by the amplifier 160 and then fed to the adaptive filter 111 through the switch 200.

In that case, if the detected level is large, the amplification factor $\mu$ is made small, while if the level is small, the amplification factor $\mu$ is made large.

According to the above arrangement, only when the level detector 150 detects that the level of the signal $[S+n_0]$ is smaller than a certain "threshold value" is the adaptive signal processing is performed by the adaptive filter 111 or the like.

Accordingly, this embodiment achieves substantially the same effect as that of the first embodiment, and since no useless power is consumed or the like, the adaptive signal processing is performed effectively.

In this case, the switch 200 is not always provided.

On the other hand, as will be seen from FIG. 4, the arrangement of the third embodiment in which the pickup 113 detects the vibration of the desk 106 is effective when the desk 106 is tapped and so on or particularly when an inadvertent vibration is produced as the noise signal $n_0$ from the microphone 103.

That is, although the case may occur that the main audio signal S can not be distinguished due to the inadvertent noise signal $n_0$, by supplying the output signal of the pickup 113 to the adaptive filter 111 as the reference signal $n_1$, the noise signal $n_0$ can be almost completely removed, so that the audio signal S is satisfactorily reproduced.

Other embodiments of the microphone apparatus according to the present invention will now be described with reference to the following drawings.

Figure 8:
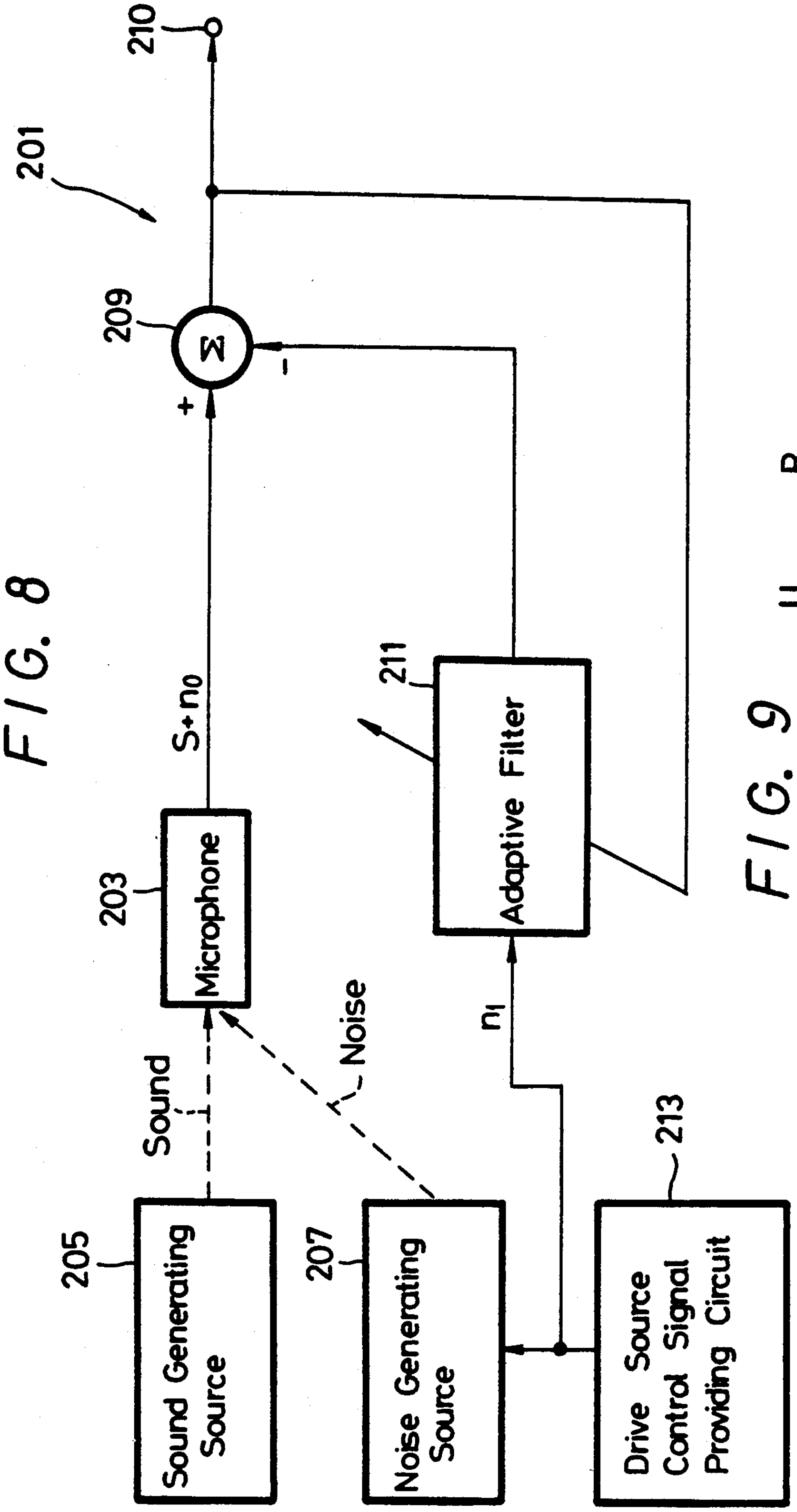
FIG. 8 is a schematic diagram showing an arrangement of a fourth embodiment of the microphone apparatus according to the present invention.

FIG. 8 generally shows a schematic diagram of a fourth embodiment of the microphone apparatus 201 according to the present invention.

As shown in FIG. 8, a microphone 203 picks up a desired sound such as human voice or the like from a sound generating source 205 and produces an audio signal S. The microphone 203 also picks up noise generated from a mechanical system 207 and produces a noise signal $n_0$.

The audio signal S and the noise signal $n_0$ are added and supplied to an adder 209, and an output of the adder 209 is supplied through a terminal 210 to a recording system not shown and also to an adaptive filter 211.

A control signal $n_1$ is used to control a drum drive motor (drive source) of the mechanical system 207 of a video tape recorder having a built-in camera or the like and supplied from a drive source control signal providing circuit 213 to the motor of the mechanical system 207 and also to the adaptive filter 211.

Figure 9:
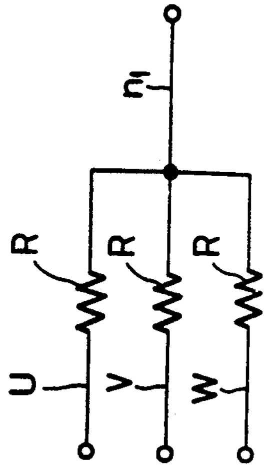
FIG. 9 is a schematic diagram used to explain a noise signal and a reference signal.

In that case, the motor is controlled by three-phase electrical signals U, V and W as will be seen from FIG. 9, and a signal (trapezoidal wave), which results from mixing these signals U, V and W by resistors R (100 kΩ), is supplied to the adaptive filter 211 as a reference signal $n_1$, so that the adaptive filter 211 produces an output of opposite phase, which is fed to the adder 209.

The reference signal $n_1$ may be a counter electromotive force of the mixed signal of the three signals U, V and W.

Figure 10:
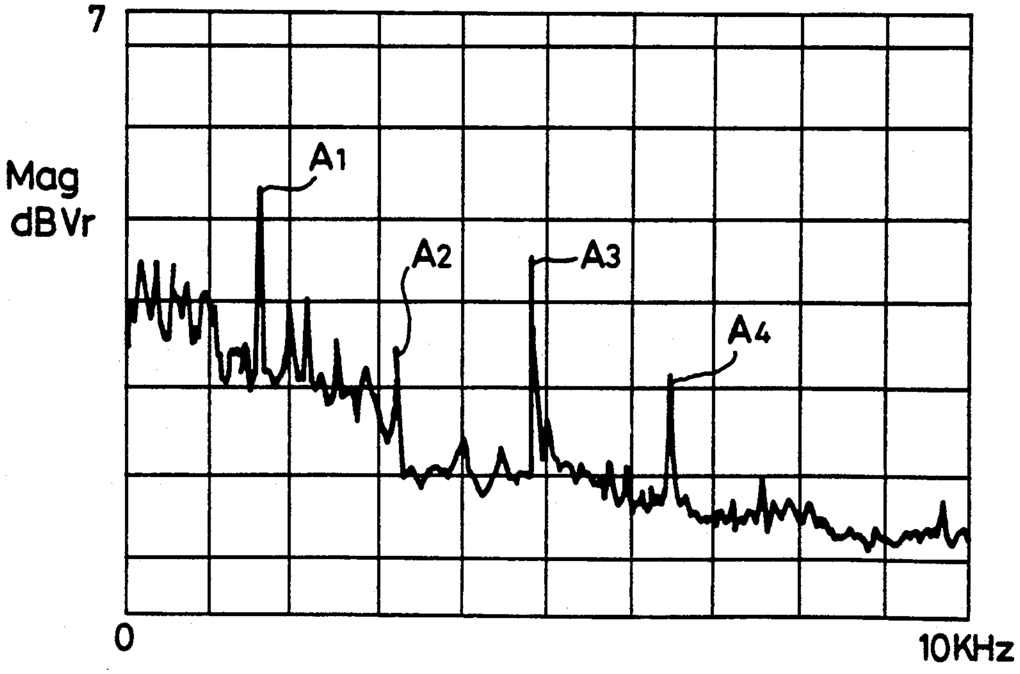
FIG. 10 is a correlative diagram showing a spectrum provided when a video tape recorder having a built-in camera is in the recording mode.
Figure 11:
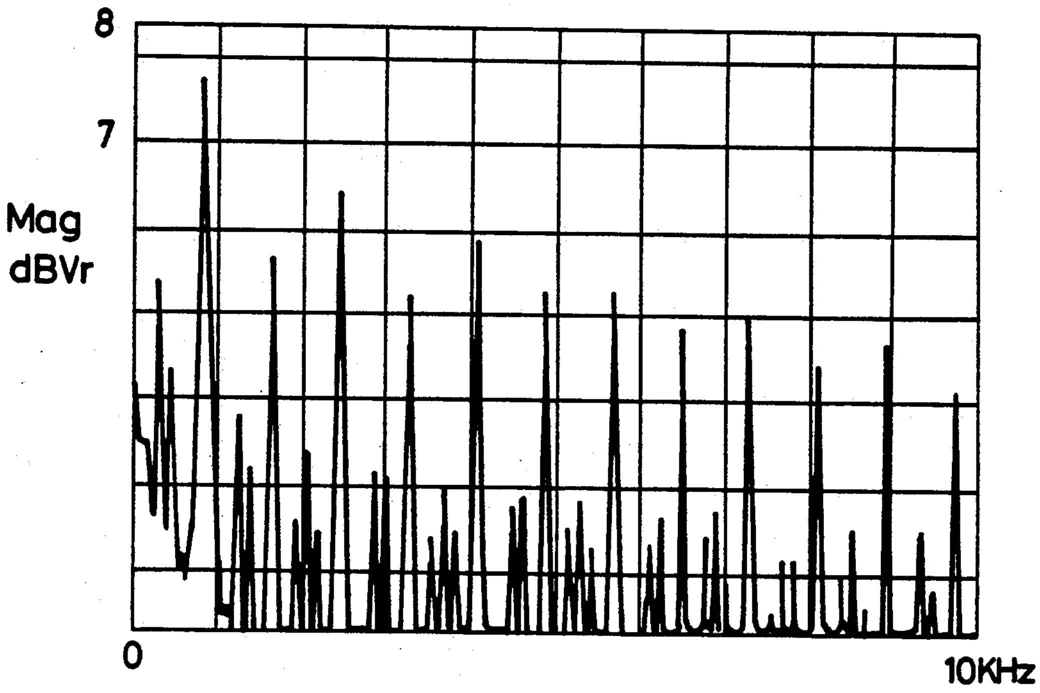
FIG. 11 is a correlative diagram showing a spectrum of the signal $n_1$.
Figure 12:
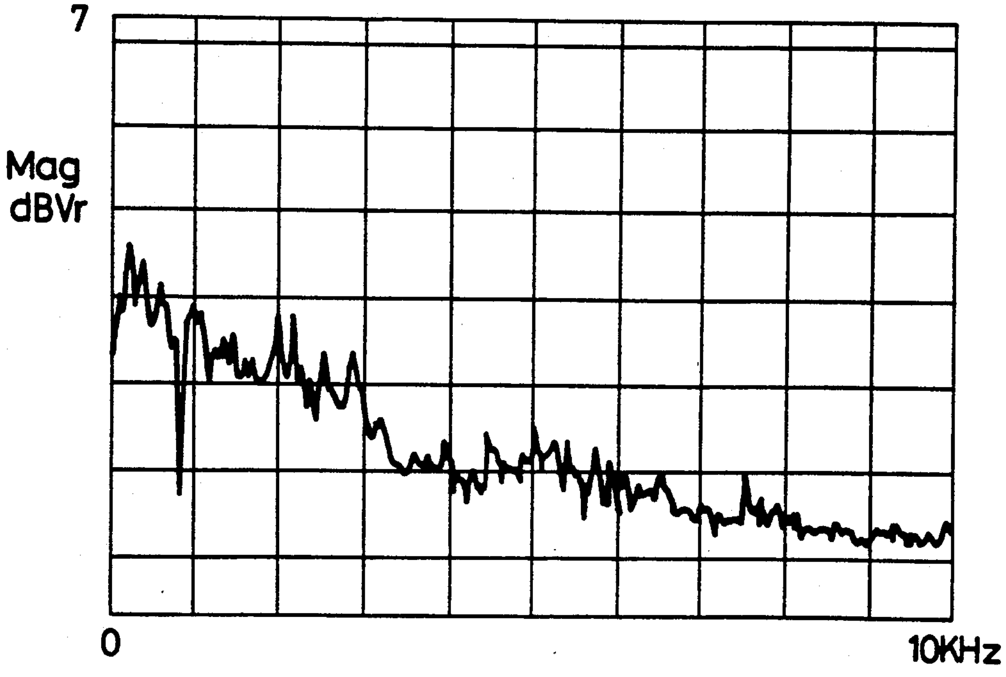
FIG. 12 is a correlative diagram showing a spectrum of a signal processed by an adaptive signal processing circuit.

As seen from FIG. 10, when the video tape recorder having a built-in camera is in the recording mode, a noise signal $n_0$ of a spectrum having peak values $A_1$, $A_2$, $A_3$ and $A_4$ is produced, and a spectrum of the mixed signal $n_1$ has a plurality of peak values as seen from FIG. 11. However, as a result of the adaptive signal processing in the adaptive filter 211 (adaptive signal processing unit) or the like, the peak values $A_1$, $A_2$, $A_3$ and $A_4$ are removed from the spectrum of the noise signal $n_0$ from the video tape recorder having a built-in camera as will be understood from FIG. 12.

As described above, according to the fourth embodiment, the motor control signal is used as the reference signal $n_1$ and the peak values $A_1$, $A_2$, $A_3$ and $A_4$ of the noise signal $n_o$ are removed by the adaptive signal processing unit such as by the adaptive filter 211 or the like. As a result, the noise signal $n_0$ is properly reduced and the audio signal is satisfactorily reproduced.

Figure 13:
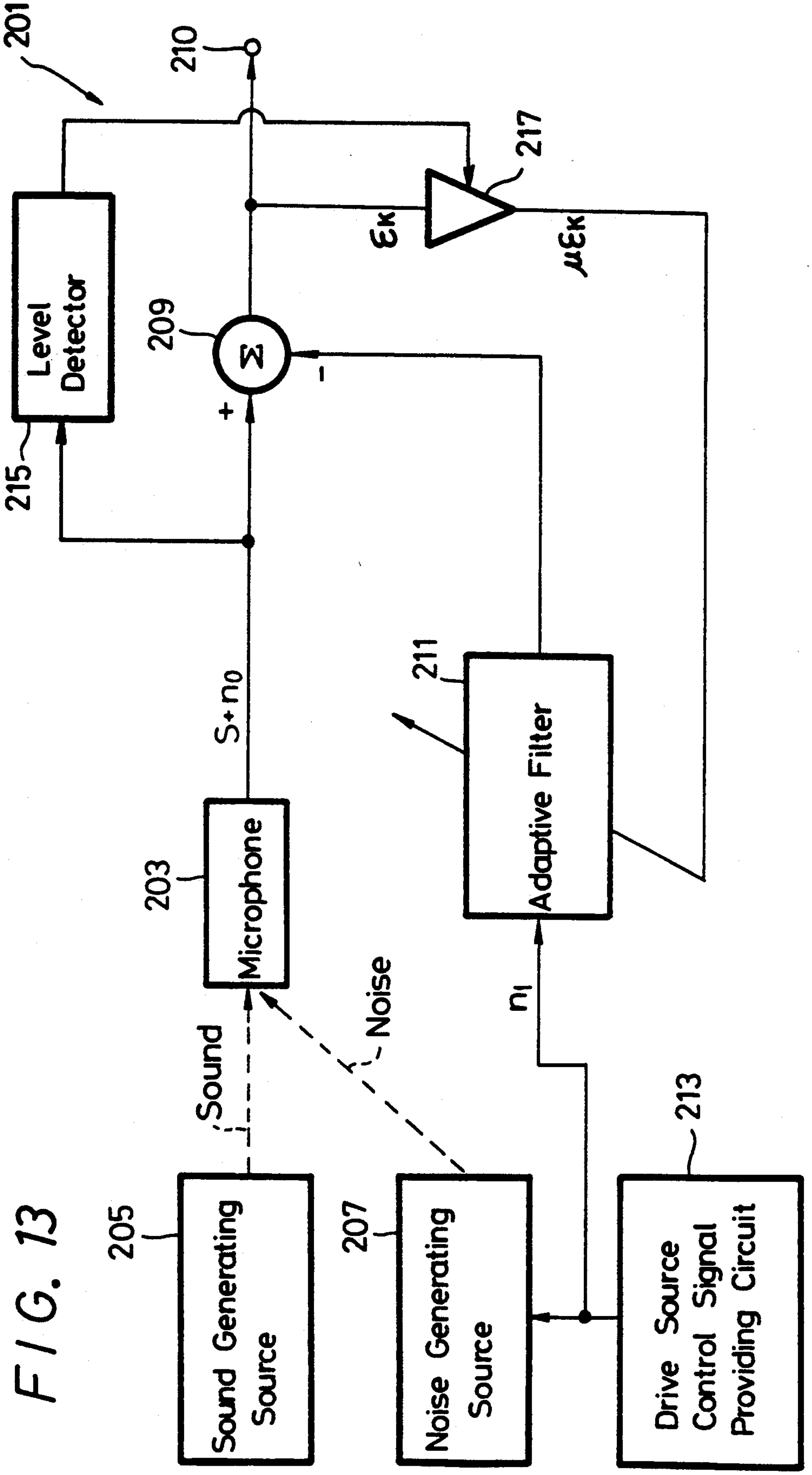
FIG. 13 is a schematic diagram showing an arrangement of a fifth embodiment of the microphone apparatus according to the present invention.

A fifth embodiment of the microphone apparatus according to the present invention will be described with reference to FIG. 13. In FIG. 13, like parts corresponding to those of FIG. 8 are marked with the same references and therefore need not be described in detail.

Even though the reproduced sound from the speaker contains, for example, both musical sound and noise, human auditory sense generally cannot distinguish the noise from the musical sound if the volume of the musical sound exceeds a certain level.

Accordingly, in such case, the adaptive signal processing is not necessarily perform and it is also appropriate to perform the adaptive signal processing only when the level of musical sound or the level of the audio signal S is below a certain level.

Therefore, according to the fifth embodiment, the adaptive signal processing is performed only when the level of the audio signal (containing the noise signal $n_0$) is below a certain "threshold value".

In that case, the level of the "threshold value" is properly selected or set in accordance with the kind (human voice, music and so on) of the audio signal S.

As will be seen from FIG. 13, in the fifth embodiment, the output of the microphone 203 is supplied to a level detector 215, wherein the level thereof is detected, and the output of the level detector 215 is supplied to an amplifier 217, changing the amplification factor $\mu$ of the amplifier 217. Then, the output $\epsilon k$ of the adder 209 is amplified into $\mu\epsilon k$ by the amplifier 217 and supplied to the adaptive filter 211.

In this case, if the detected level is large, the amplification factor $\mu$ is made small, while if the detected level is small, the amplification factor $\mu$ is made large.

According to the above arrangement, only when the level detector 215 detects that the level of the signal $[S+n_0]$ is smaller than a certain "threshold value", is the adaptive signal processing is performed by the adaptive filter 211 or the like.

Accordingly, this embodiment has the same effect as that of the preceding embodiments, and since no useless power or the like is consumed, the adaptive signal processing can be performed effectively.

While in the above embodiments the present invention is applied to a video tape recorder having a built-in camera and and auto-focusing motor, the zoom motor or the mechanical unit serving as the example of the vibration generating source, the present invention is not limited thereto and may be applied to a standard tape recorder.

According to the microphone apparatus of the present invention, as will be understood from the above description, the vibration detected signal of the vibration from the vibration generating source which generates noise within or outside of the recorder is used for the reference signal, and the adaptive signal processing is performed.

Therefore, an unnecessary noise signal is sufficiently removed, thus the noise signal being properly reduced.

Furthermore, in the microphone apparatus of the present invention, the drive source control signal of the recorder is used for the reference signal to thereby perform the adaptive signal processing. Therefore, the unnecessary noise signal is sufficiently removed, and the noise is properly reduced.

Having described the preferred embodiments of the invention with reference to the accompanying drawings, it is to be understood that the invention is not limited to those precise embodiments and that various changes and modifications thereof could be effected by one skilled in the art without departing from the spirit or scope of the novel concepts of the invention as defined in the appended claims.

We claim as our invention:

1. A microphone apparatus comprising:

a microphone for picking up sounds and producing an output audio signal therefrom;

vibration detecting means for producing a vibration detection signal in response to vibrations of a vibration generating source that are also picked up by said microphone, so that an unnecessary noise signal is included in said output audio signal produced by said microphone, said vibrating generating source operating in response to a drive signal fed thereto;

adaptive signal processing means supplied with said vibration detected signal as a reference signal and producing a signal for combining with said output audio signal and reducing said unnecessary noise signal contained therein;

control means for controlling operation of said adaptive signal processing means when a detected level of the output audio signal from said microphone becomes less than a predetermined threshold level; and a switch connected to said drive signal and said adaptive signal processing means for controlling said adaptive signal processing means to produce said signal for combining with said output audio signal only in the presence of said drive signal.

2. A microphone apparatus comprising:

a microphone for supplying a desired audio signal to a recording apparatus having a mechanical driving unit operative in response to a drive control signal;

adaptive signal processing means for reducing an unnecessary noise signal included with the desired audio signal and based on noise generated from said mechanical driving unit that it picked up by said microphone on the basis of a reference signal, wherein said adaptive signal processing means receives as said reference signal the drive control signal supplied to said mechanical drive unit; and control means for controlling operation of said adaptive signal processing means when a detected level of the output audio signal from said microphone becomes less than a predetermined threshold level.

3. An audio circuit in a recording apparatus having a recording mechanism for recording an audio signal output from a microphone, comprising:

vibration detecting means for producing a vibration detected signal in response to vibrations of a vibration generating source picked up by said microphone that result in an unnecessary noise signal included with said audio signal from the microphone, said vibration generating source producing vibrations in response to a drive signal;

adaptive signal processing means supplied with said vibration detected signal as a reference signal and producing a signal for combining with the audio signal output from the microphone for reducing said unnecessary noise signal contained in said audio signal;

control means for controlling operation of said adaptive signal processing means when a detected level of the audio output signal from said microphone becomes less than a predetermined threshold level; and a switch connected to said drive signal and said adaptive signal processing means for controlling said adaptive signal processing means to produce said signal for combining with the audio signal output from the microphone only in the presence of said drive signal.

4. An audio circuit in a recording apparatus according to claim 3, further comprising means for arranging said noise detecting means in the vicinity of a driving source that drives a movable unit of said recording apparatus and that comprises said vibration generating source.

5. An audio circuit in a recording apparatus having a mechanical driving unit and a recording mechanism for recording an output signal from a microphone comprising:

adaptive signal processing means for reducing an unnecessary noise signal included in the output signal of the microphone and based on noise generated from said mechanical driving unit that is picked up by said microphone, said adaptive signal processing means operating in response to a reference signal, wherein said adaptive signal processing means receives as said reference signal a control signal supplied to the mechanical driving unit of said recording apparatus; and control means for controlling operation of said adaptive signal processing means when a detected level of the output signal from said microphone becomes less than a predetermined threshold level.

* * * * *

UNITED STATES PATENT AND TRADEMARK OFFICE

CERTIFICATE OF CORRECTION

PATENT NO. : 5,243,661

DATED : September 7, 1993

INVENTOR(S) : Masashi Ohkubo, et al

It is certified that error appears in the above-indentified patent and that said Letters Patent is hereby corrected as shown below:

Col. 1, line 31, delete "the"
line 51, change "W:" to --$W_k$--
Col. 2, line 6, change "to produce" to --that produces--
Col. 4, line 13, change "n;" to --$n_1$--
line 31, change "shown" to --show--

Col. 7, line 29, change "detection" to --detected--
line 58, change "it" to --is--

Signed and Sealed this

Twenty-fifth Day of October, 1994

Attest:

Bruce Lehman

BRUCE LEHMAN

Attesting Officer

Commissioner of Patents and Trademarks